(12) United States Patent
Lee et al.

(10) Patent No.: US 10,682,075 B2
(45) Date of Patent: Jun. 16, 2020

(54) DRY EYE SYNDROME ALERT SYSTEM THROUGH POSTURE AND WORK DETECTION

(71) Applicant: SEOUL NATIONAL UNIVERSITY R&DB FOUNDATION, Seoul (KR)

(72) Inventors: Min Ho Lee, Gimpo-si (KR); Woo Jin Park, Seoul (KR); Seung Won Baek, Gimpo-si (KR); Hae Seok Jeong, Incheon (KR); Taek Beom Yoo, Seoul (KR); Yoon Jin Lee, Daejeon (KR); Hae Hyun Lee, Seoul (KR); Byoung Hyun Choi, Seoul (KR); Soo Min Hyun, Suwon-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/342,202

(22) PCT Filed: Oct. 18, 2017

(86) PCT No.: PCT/KR2017/011558
§ 371 (c)(1),
(2) Date: Apr. 16, 2019

(87) PCT Pub. No.: WO2018/074853
PCT Pub. Date: Apr. 26, 2018

(65) Prior Publication Data
US 2019/0239774 A1 Aug. 8, 2019

(30) Foreign Application Priority Data
Oct. 18, 2016 (KR) .......... 10-2016-0135285

(51) Int. Cl.
*G08B 23/00* (2006.01)
*A61B 5/11* (2006.01)
(Continued)

(52) U.S. Cl.
CPC .......... *A61B 5/1103* (2013.01); *A61B 5/1116* (2013.01); *G08B 5/36* (2013.01);
(Continued)

(58) Field of Classification Search
CPC ..... A61B 5/1103; A61B 5/1116; A61B 5/163; A61B 5/6897; A61B 2503/24; G08B 5/36; G08B 21/04; G08B 21/18; G08B 23/00
(Continued)

(56) References Cited

U.S. PATENT DOCUMENTS 6,304,187 B1 10/2001 Pirim
9,846,955 B2 * 12/2017 Lee .......................... G06T 11/60
(Continued)

FOREIGN PATENT DOCUMENTS

| KR | 10-2012-0021550 A | 3/2012 |
| KR | 10-2015-0004524 A | 1/2015 |
| KR | 10-1546249 B1 | 8/2015 |

OTHER PUBLICATIONS

International Search Report for PCT/KR2017/011558 dated May 31, 2018 from Korean Intellectual Property Office.
(Continued)

*Primary Examiner* — Zhen Y Wu
(74) *Attorney, Agent, or Firm* — Revolution IP, PLLC

(57) ABSTRACT

A dry eye syndrome alert system through posture and work detection, includes: a data collecting unit configured to detect a posture of a user to collect posture data of the user and preprocess the posture data; an eye blink frequency calculating unit configured to identify a posture change of the user on the basis of the posture data, calculate a motion variability on the basis of the posture change, and estimate an eye blink frequency of the user on the basis of the motion variability; and a diagnosis and alert output unit configured
(Continued)

to store data regarding the estimated eye blink frequency, compare the estimated eye blink frequency with a preset reference value, and output an alert to the user when the estimated eye blink frequency is less than or equal to the preset reference value.

8 Claims, 3 Drawing Sheets

(51) Int. Cl.
*G08B 21/18* (2006.01)
*G08B 21/04* (2006.01)
*G08B 5/36* (2006.01)
*A61B 5/16* (2006.01)
*A61B 5/00* (2006.01)

(52) U.S. Cl.
CPC ............. *G08B 21/04* (2013.01); *G08B 21/18* (2013.01); *A61B 5/163* (2017.08); *A61B 5/6897* (2013.01); *A61B 2503/24* (2013.01); *G08B 23/00* (2013.01)

(58) Field of Classification Search
USPC ...................................... 340/573.1
See application file for complete search history.

(56) References Cited

U.S. PATENT DOCUMENTS

| | | | | |
|---|---|---|---|---|
| 2008/0187175 A1* | 8/2008 | Kim | ................... | G06K 9/00268 382/103 |
| 2008/0221401 A1* | 9/2008 | Derchak | ................... | A61B 5/16 600/301 |
| 2010/0014711 A1* | 1/2010 | Camhi | ................... | B60K 28/06 382/104 |
| 2011/0080290 A1 | 4/2011 | Baxi et al. | | |
| 2012/0032806 A1 | 2/2012 | Lee | | |
| 2013/0012789 A1* | 1/2013 | Horseman | ............ | A61B 5/6887 600/301 |
| 2014/0058703 A1* | 2/2014 | Kimishima | ......... | G06F 19/3481 702/177 |
| 2014/0152792 A1* | 6/2014 | Krueger | ................ | A61M 21/00 348/78 |
| 2015/0374236 A1* | 12/2015 | Wu | .......................... | A61B 3/18 351/209 |
| 2016/0148050 A1* | 5/2016 | Lee | .................... | G06K 9/00845 348/78 |
| 2016/0345818 A1* | 12/2016 | Suzuki | ................. | A61B 3/0025 |
| 2016/0373645 A1* | 12/2016 | Lin | .................... | H04N 5/23219 |
| 2016/0374594 A1* | 12/2016 | Garcia Molina | .... | A61B 5/1103 600/558 |
| 2017/0169715 A1* | 6/2017 | Alyuz Civitci | ........ | G06N 20/00 |
| 2017/0188823 A1* | 7/2017 | Ganesan | ................ | A61B 3/113 |
| 2017/0316240 A1* | 11/2017 | Tiberi | .................... | G06Q 10/20 |
| 2017/0330440 A1* | 11/2017 | Sato | .......................... | F21S 6/00 |
| 2018/0012090 A1* | 1/2018 | Herbst | ............... | G06K 9/00845 |
| 2018/0239975 A1* | 8/2018 | Tamrakar | ........... | G06K 9/00261 |
| 2019/0155279 A1* | 5/2019 | Tayama | ................ | B60W 50/14 |

OTHER PUBLICATIONS

Debra A. Schaumberg et al., "Prevalence of dry eye syndrome among US women", American Journal of Ophthalmology, Aug. 2003; 136(2): 318-326.

Ashley Behrens et al., "Dysfunctional Tear Syndrome A Delphi Approach to Treatment Recommendations", Cornea, vol. 25, No. 8, Sep. 2006: 900-907.

Lemp MA et al., "The Definition and Classification of Dry Eye Disease: Report of the Definition and Classification Subcommittee of the International Dry Eye Work Shop (2007)", The Ocular Surface, Apr. 2007, vol. 5, No. 2; 75-92.

\* cited by examiner

US 10,682,075 B2

DRY EYE SYNDROME ALERT SYSTEM THROUGH POSTURE AND WORK DETECTION

TECHNICAL FIELD

The present invention relates to a system for alerting a user to dry eye syndrome through posture and work detection, and more specifically, to a system for alerting a user, that is, a person who sits on a chair and studies or performs tasks or affairs, so that the user naturally blink his/her eyes by an unconditioned reflex action in order to prevent dry eye syndrome due to insufficient eye blink.

BACKGROUND ART

An eye is largely divided into an eyeball and ocular adnexa. The eyeball includes an outer membrane, a middle membrane, an inner membrane, and contents, and the ocular adnexa includes an orbit of an eye, a conjunctiva, and the like. Among these, the outer membrane and the conjunctiva form a boundary between the eye and the outer world.

The cornea is a transparent membrane that forms the surface of the eyeball. The conjunctiva is a mucosal membrane that connects the eyeball with an eyelid and is divided into a conjunctiva palpebrarum and a bulbar conjunctiva. Meanwhile, a transition part of the cornea and the bulbar conjunctiva is referred to as a limbus corneae, and a transition part of the bulbar conjunctiva and the conjunctiva palpebrarum is referred to as a fornix conjunctiva.

Dry eye syndrome, also known as keratoconjunctivitis sicca or dysplasia, is a common disease, which is a type of ophthalmic disorder, affecting a large number of people. In the United States, approximately 5 million people among a population over the age of 50 are estimated to have severe dry eye syndrome (Schaumberg et al., Am J Ophthalmol 2003; 136 (2): 318-326).

Symptoms of dry eye syndrome include burning, dryness, redness, itching, persistent irritation, and the like. Dry eye syndrome, when severe, may damage eyesight and cause difficulty in performing vision-critical tasks, such as studying, reading, and driving. Dry eye syndrome may be a symptom of other diseases, rather than mere dry eye syndrome itself. Typically, the symptoms may be manifested in Sjögren's syndrome. In addition, with age, moisture of the lacrimal gland may decrease, which leads to eye dryness, congestion, itching, and a foreign object feeling, therefore dry eye syndrome often appears as a symptom of aging.

Dry eye syndrome is a multifactorial disorder that is accompanied by symptoms of eye discomfort, visual disturbance, instability of the tear film, and damage of the ocular surface caused by an insufficient amount of tears or abnormality of a tear component, involving an increase in the tear film osmolarity and inflammation on the ocular surface (an increase in inflammatory cytokines) (Behrens A, Doyle J J, Stern L, et al.; Dysfunctional tear syndrome study group. Dysfunctional tear syndrome: a Delphi approach to treatment recommendations. Cornea 2006; 25: 900-907), (Lemp M A, Baudouin C, Baum J, et al. The definition and classification of dry eye disease: report of the definition and classification subcommittee of the international dry eye workshop (2007). Ocul Surf 2007; 5: 75-92).

Various methods of treating dry eye syndrome are known. Dry eye syndrome is managed with nonpharmacologic treatments including exacerbating factor avoidance, eyelid hygiene, tear supplementation, secretagogues, a punctual plug, an anti-inflammatory agent, a moisture chamber, and other environmental management and pharmacologic treatments (Behrens et al., Dysfunctional tear syndrome study group. Dysfunctional tear syndrome: a Delphi approach to treatment recommendations. Cornea 2006; 25(8): 900-907).

Among the various methods of treating dry eye syndrome, pharmacological treatment is accompanied by many shortcomings. For example, artificial tear solutions are very cumbersome to use due to having highly temporary effects, which requires the patient to repeatedly administer the artificial solution. In addition, increasing the viscosity of the artificial tear solution may prolong the duration of the artificial tear solution in the eyeball but may cause stickiness in the eyes, which in turn leads to deterioration of feeling in use. In addition, administration of topical steroids leads to development of side effects, such as increased intraocular pressure, glaucoma, cataracts, and worsening of corneal infections.

Meanwhile, eye tracker technology capable of tracking and monitoring eye movement in performing a certain affair or task has been introduced.

However, such an eye tracker is inconvenient due to the need for wearing, attaching, or installing a separate device, so there is an imperative need to develop a technique capable of preventing dry eye syndrome without causing inconvenience to a user.

DISCLOSURE

Technical Problem

The present invention is directed to providing a system for alerting dry eye syndrome through posture and work detection which is capable of preventing a user performing a certain affair or task from having dry eye syndrome due to a decrease in the eye blink frequency due to focusing attention on the affair or task for a long period of time.

The present invention is directed to providing a method capable of preventing dry eye syndrome through posture and work detection using the system.

Technical Solution

One aspect of the present invention provides a system for alerting dry eye syndrome through posture and work detection that includes a data collecting unit, an eye blink frequency calculating unit, and a diagnosis and alert output unit, in which in order to prevent office workers (hereinafter, referred to as 'workers' or 'users') who are working while being seated, some of whom perform an active task requiring intense focus or some of whom have a high level of movement during work, from having dry eye syndrome due to a decrease in the eye blink rate when performing the affairs or tasks, detects a posture of the user and a task performed by the user and alerts the user so that the user frequently blinks his/her eyes, thereby compensating for the insufficient eye blink.

Another aspect of the present invention provides a system for alerting dry eye syndrome through posture and work detection that includes: a data collecting unit configured to detect a posture of a user to collect posture data of the user and preprocess the posture data; an eye blink frequency calculating unit configured to identify a posture change of the user on the basis of the posture data, calculate a motion variability on the basis of the posture change, and estimate an eye blink frequency of the user on the basis of the motion variability; and a diagnosis and alert output unit configured to store data regarding the estimated eye blink frequency, compare the estimated eye blink frequency with a preset reference value, and output an alert to the user when the estimated eye blink frequency is less than or equal to the preset reference value.

In one example, data transmission and reception between the data collecting unit, the eye blink frequency calculating unit, and the diagnosis and alert output unit may be performed in a wireless or wired communication method.

The data collecting unit may include a sensor unit configured to detect the posture of the user to collect the posture data of the user and a preprocessing unit configured to preprocess the posture data.

The eye blink frequency calculating unit may include a motion variability calculating unit configured to identify the posture change of the user on the basis of the posture data and calculate the motion variability on the basis of the posture change and an eye blink frequency estimating unit configured to estimate the eye blink frequency of the user on the basis of the motion variability.

The diagnosis and alert output unit may include a diagnosis unit configured to store frequency data regarding the eye blink frequency, and compare the frequency data with a preset reference value to determine whether the eye blink frequency is less than or equal to the preset reference value; and an alert output unit configured to output an alert to the user when the eye blink frequency is less than or equal to the preset reference value.

The sensor unit may include a plurality of pressure sensors disposed on a seat of a chair and a plurality of distance sensors disposed on a backrest of the chair.

The work state detecting unit may be software that is installed in a smart device of the user to identify a program operated by the user in the smart device.

Here, the 'smart device' may refer to a product which changes a large part of a function or adds another function through applications included in a smart television (smart TV), a smart phone, a tablet personal computer (table PC), a notebook computer, or the like.

The motion variability calculating unit may calculate the motion variability of the user on the basis of a change in pressure data measured through the plurality of pressure sensors and interval data between a back of the user and the backrest measured through the plurality of distance sensors.

The eye blink frequency estimating unit may estimate the eye blink frequency of the user by matching the motion variability with eye blink frequency quantified data that is stored in advance.

The alert output unit may be disposed on any one of an armrest of a chair and a smart device of the user.

Advantageous Effects

According to the present invention, in order to prevent dry eye syndrome caused by decrease in an eye blink rate while performing affairs or tasks, the system for alerting dry eye syndrome through posture and work detection and method of preventing dry eye syndrome through posture and work detection can detect a posture of the user and a task performed by the user on the basis of the posture and alert the user so that the user frequently blinks his/her eyes to compensate for insufficient eye blink, thereby effectively preventing the user from having dry eye syndrome.

The system for alerting dry eye syndrome through posture and work detection and method of preventing dry eye syndrome through posture and work detection can be effectively used for eye care of students or businessman.

Eye blink frequency information provided by the present invention can be fed back to a user so that the user develops a habit that reduces dry eye syndrome.

BEST MODES OF THE INVENTION

Figure 1:
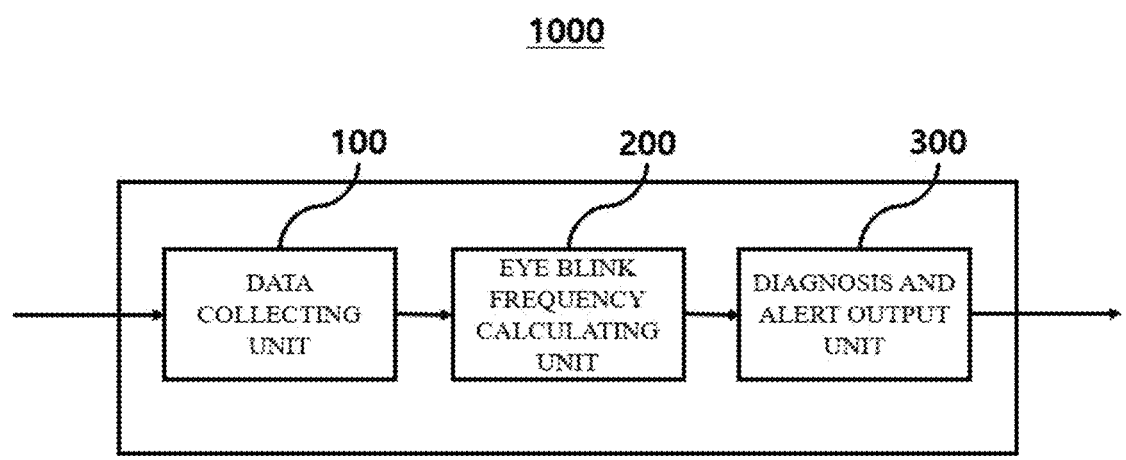
FIG. 1 is a conceptual diagram for describing a system for alerting dry eye syndrome through posture and work detection according to an embodiment of the present invention.

While the present invention is susceptible to various modifications and alternative embodiments, specific embodiments thereof are shown by way of example in the accompanying drawings and will be described. However, it should be understood that there is no intention to limit the present invention to the particular embodiments disclosed, but on the contrary, the present invention is to cover all modifications, equivalents, and alternatives falling within the spirit and scope of the present invention.

Hereinafter, example embodiments of the present invention will be described with reference to the accompanying drawings in detail. The same reference numerals are used to refer to the same elements through the description of the figures.

Figure 2:
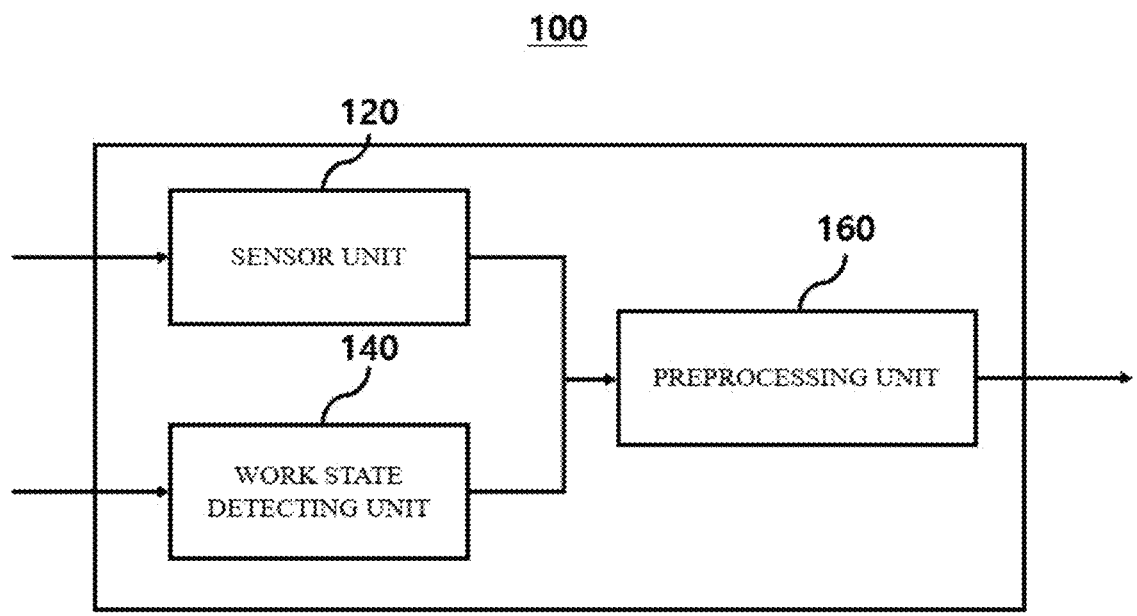
FIG. 2 is a conceptual diagram for describing a data collecting unit according to an embodiment of the present invention.
Figure 3:
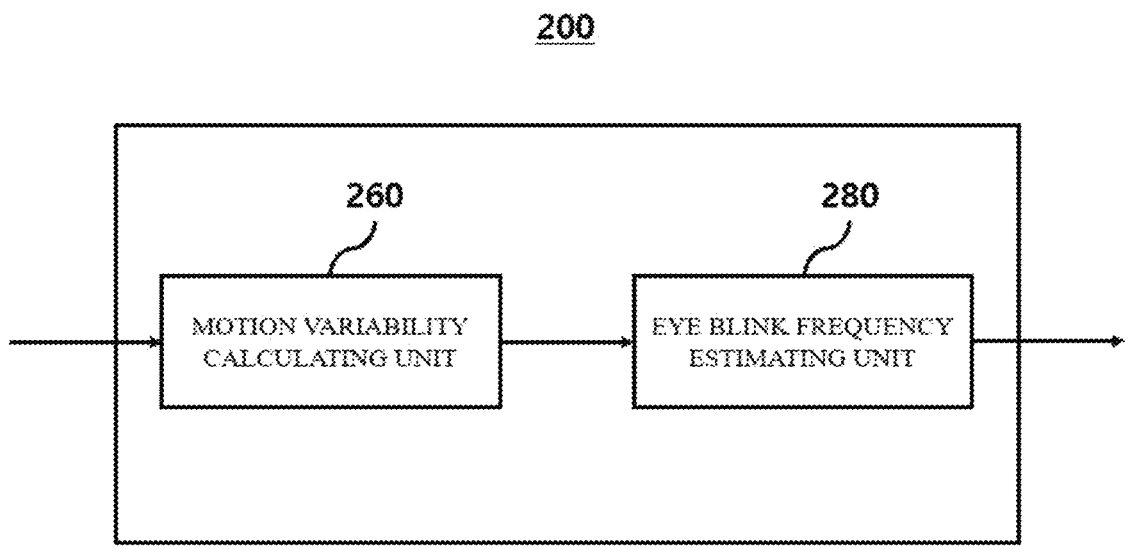
FIG. 3 is a conceptual diagram for describing an eye blink frequency calculating unit according to an embodiment of the present invention.
Figure 4:
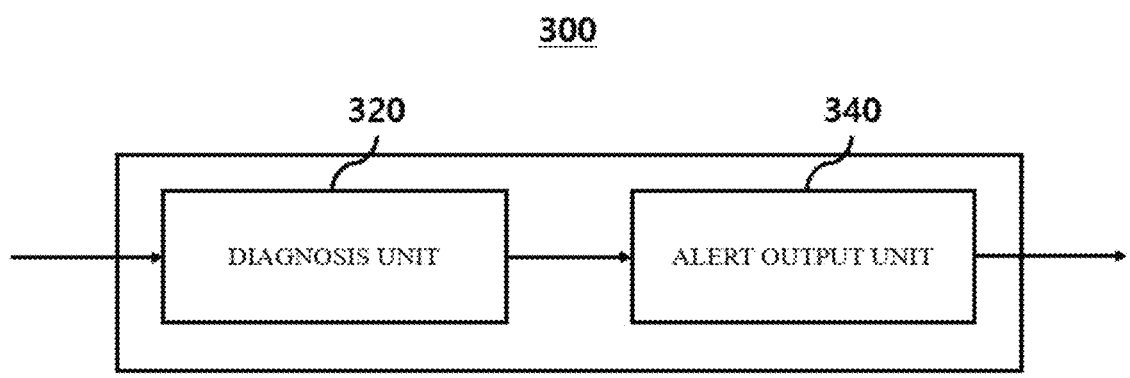
FIG. 4 is a conceptual diagram for describing a diagnosis and alert output unit according to an embodiment of the present invention.
Figure 5:
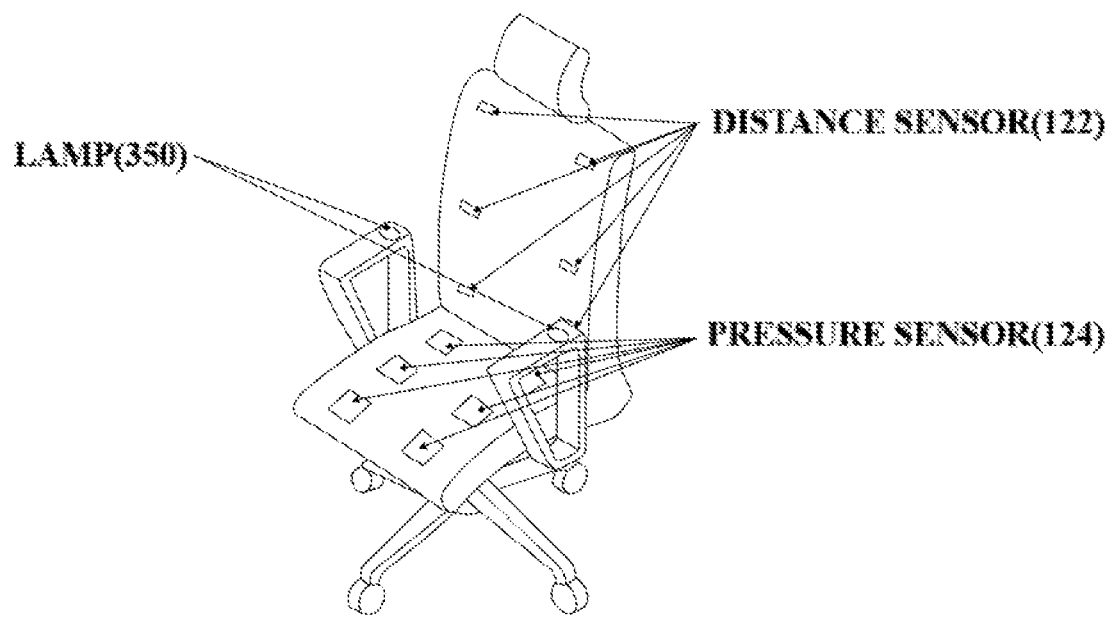
FIG. 5 is a view for describing an example of placement of a pressure sensor, a distance sensor, and an alert output unit on a chair according to an embodiment of the present invention.
Figure 6:
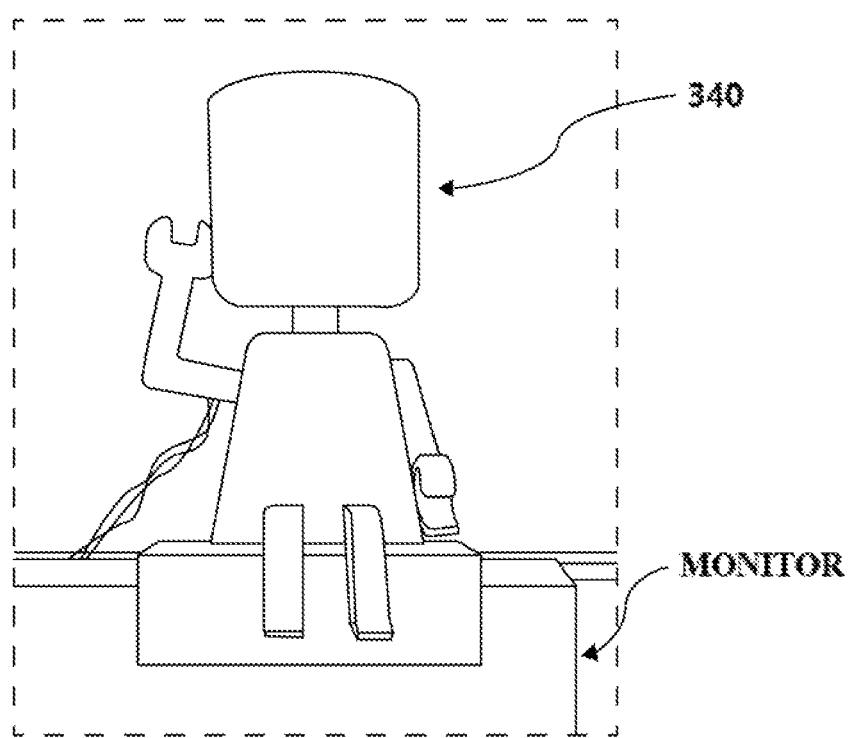
FIG. 6 is a photograph for describing an example of an arrangement of an alert output unit according to an embodiment of the present invention.

FIG. 1 is a conceptual diagram for describing a system for alerting dry eye syndrome through posture and work detection according to an embodiment of the present invention, FIG. 2 is a conceptual diagram for describing a data collecting unit according to an embodiment of the present invention, FIG. 3 is a conceptual diagram for describing an eye blink frequency calculating unit according to an embodiment of the present invention, FIG. 4 is a conceptual diagram for describing a diagnosis and alert output unit according to an embodiment of the present invention, FIG. 5 is a view for describing an example of placement of a pressure sensor, a distance sensor, and an alert output unit on a chair according to an embodiment of the present invention, and FIG. 6 is a photograph for describing an example of an arrangement of an alert output unit according to an embodiment of the present invention.

Referring to FIG. 1, a system 1000 for alerting dry eye syndrome through posture and work detection according to the embodiment of the present invention includes a data collecting unit 100, an eye blink frequency calculating unit 200, and a diagnosis and alert output unit 300.

The data collecting unit 100 may detect a posture and a work state of a user to collect posture data and work state data of the user and may preprocess the posture data and the work state data. To this end, referring to FIG. 2, the data collecting unit 100 may include a sensor unit 120, a work state detecting unit 140, and a preprocessing unit 160.

The sensor unit 120 may collect the posture data of the user by sensing the posture of the user. For example, referring to FIG. 5, the sensor unit 120 may include a plurality of pressure sensors 124 disposed on a seat of a chair and a plurality of distance sensors 124 disposed on a backrest of the chair.

The plurality of pressure sensors 124 may be disposed at equal intervals on the seat of the chair, but the arrangement of the pressure sensors 124 may vary according to the user's body structure, such as the user's physique, the user's gender, and the like.

The plurality of distance sensors 122 may be disposed at equal intervals on the backrest of the chair, but the arrangement of the distance sensors 122 may vary according to the user's body structure, such as the user's physique, the user's gender, and the like.

An area, on which pressure is concentrated and which is a part of the entire area of the seat, may be identified using pressure data measured through the plurality of pressure sensors 124, and interval data between a user's back and the backrest measured through the plurality of distance sensors 122 may be identified.

For example, when the area on which pressure is concentrated is a front portion of the seat of the chair and the interval between the user's back and the backrest is great, the user may be identified as having a posture leaning toward a front portion of the chair, and in the opposite case, the user may be identified as having a posture leaning toward a rear portion of the chair. In this manner, the postures of the user may be classified. In addition, the posture data of the user may be used to identify the degree of posture change, and the degree of posture change may be used to calculate a motion variability. The motion variability may refer to the degree of posture change of the user over time.

The work state detecting unit 140 may collect work state data of the user by detecting the work state of the user. To this end, the work state detecting unit 140 may be implemented using software that is installed in a smart device of the user to identify a program operated by a user in the smart device.

The preprocessing unit 160 may preprocess the posture data and the work state data. Preprocessing may refer to a process of converting the posture data and the work state data into data suitable for calculating a motion variability and, for example, may be performed by a process of missing value supplement, outliner exclusion, form transformation, data integration, and the like.

The eye blink frequency calculating unit 200 may classify the postures of the user on the basis of the posture data. In addition, the eye blink frequency calculating unit 200 may calculate the motion variability on the basis of the posture change of the user and may classify the work state of the user on the basis of the work state data.

In addition, the eye blink frequency calculating unit 200 may estimate the eye blink frequency of the user on the basis of at least one of the classified posture, the classified work state, and the motion variability.

For example, by identifying whether a user is using the Internet with a smart device or is using a program (Hangul word processor, Excel, and the like) for document editing, a work state, such as an Internet search work state, a document editing work state, or the like, may be identified.

Referring to FIG. 3, the eye blink frequency calculating unit 200 may include a motion variability calculating unit 260 and an eye blink frequency estimating unit 280.

The motion variability calculating unit 260 may calculate a motion variability of a user on the basis of a posture change of the user. For example, the motion variability calculating unit 260 may calculate the motion variability of the user on the basis of a change in pressure data measured through the plurality of pressure sensors 124 and interval data between the user's back and the backrest measured through the plurality of distance sensors 122.

For example, when a specific portion of the seat of the chair is subject to concentrated pressure and a difference between a distance from the user's back to an upper portion of the backseat of the chair and a distance from the user's back to a lower portion of the backseat of the chair has almost no change, the motion variability of the user is calculated to be low, and when a portion being subject to concentrated pressure in the seat of the chair continuously changes, a difference between a distance from the user's back to the upper portion of the backseat of the chair and a distance from the user's back to the lower portion of the backseat of the chair continuously changes, or the distance difference exceeds a predetermined distance, the user is determined to have a high level of movement, and thus the motion variability is calculated to be high.

Considering the motion variability data together with the phenomenon that an eye blink decrease occurs when the user performs a task having a high level of movement, it may be determined that the probability of user eye blink decreasing is high when the motion variability is high.

The eye blink frequency estimating unit 280 may estimate the eye blink frequency of the user on the basis of one or more of the classified posture, the classified work state, and the motion variability. For example, the eye blink frequency estimating unit 280 may estimate the eye blink frequency of the user by matching the classified posture, the classified work state, and the motion variability with eye blink frequency quantified data that is stored in advance. The eye blink frequency may be represented as the number of eye blink times per unit time (n times/$\Delta t$).

For example, when the posture of the user is identified as leaning toward the front portion of the chair, the user may be identified as being highly focused, and therefore it may be estimated that the eye blink frequency is low. As another example, considering that an eye blink decrease occurs when an active task requiring intense focus is performed, it may be determined that a document editing work state has a higher probability of eye blink decrease compared to that of an Internet search work state.

For example, experiment data regarding a minimum number of eye blink times according to a user's motion variability may be obtained, and thus the eye blink frequency quantified data may be obtained on the basis of the data quantified by the experiment. The eye blink frequency quantified data (data regarding eye blink frequency) may be stored in the eye blink frequency estimating unit 280 in advance. The eye blink frequency estimating unit 280 may estimate the eye blink frequency of the user by matching the classified posture of the user, the classified work state of the user, and the motion variability value of the user with the eye blink frequency quantified data stored in advance.

The diagnosis and alert output unit 300 stores data regarding the estimated eye blink frequency, compares the stored data with a preset reference value, and outputs an alert to the user when the eye blink frequency is less than or equal to the reference value.

The preset reference value is data regarding a minimum number of eye blink times by which dry eye syndrome and the like is prevented and may be appropriately set on the basis of the work classification, the posture classification, and the calculated motion variability. The reference value may be changed according to surrounding environments (temperature, humidity, and the like) of the user and may be obtained by an experimental method.

Referring to FIG. 4, the diagnosis and alert output unit 300 may include a diagnosis unit 320 and an alert output unit 340.

The diagnosis unit 320 may store the frequency data regarding the estimated eye blink frequency. For example, the frequency data regarding the eye blink frequency may be stored in a cloud server or the like and may be displayed through the alert output unit 340, the smart device of the user, or the like so that the user identifies the current number of eye blink times of the user.

The diagnosis unit 320 may compare the stored frequency data with the preset reference value to diagnose whether the eye blink frequency is less than or equal to the reference value.

The alert output unit 340 may output an alert to the user when the eye blink frequency is less than or equal to the reference value.

The alert output unit 340 may be disposed on one of an armrest of a chair and a smart device of the user. For example, referring to FIG. 6, the alert output unit 340 may be disposed on an upper right end of a computer monitor used by a user and alert the user to an insufficiency of the eye blink rate through sound or a lamp light flashing from the alert output unit 340. As another example, referring to FIG. 5, a lamp 350 may be disposed on the armrest of the chair on which the user is seated and alert the user to an insufficiency of the eye blink rate by flashing a lamp light. In addition, the alert output unit 340 may be configured to display an alert phrase through a display device included in the smart device of the user or generate an alarm sound from the smart device such that the user may be notified of an insufficiency of the eye blink rate.

Although the embodiments of the present invention have been described with reference to the accompanying drawings, this is for illustrative purposes, and a person of ordinary skill in the art should appreciate that various modifications, equivalents, and other embodiments are possible without departing from the scope and sprit of the present invention. Therefore, the scope of the present invention is defined by the appended claims of the present invention.

REFERENCE NUMERALS

1000: system for alerting dry eye syndrome through posture and work detection
100: data collecting unit
200: eye blink frequency calculating unit
300: diagnosis and alert output unit

The invention claimed is:

1. A dry eye syndrome alert system through posture and work detection comprising:
a data collecting unit configured to detect a posture of a user to collect posture data of the user and preprocess the posture data;
an eye blink frequency calculating unit configured to identify a posture change of the user on the basis of the posture data, calculate a motion variability on the basis of the posture change, and estimate an eye blink frequency of the user on the basis of the motion variability; and
a diagnosis and alert output unit configured to store data regarding the estimated eye blink frequency, compare the estimated eye blink frequency with a preset reference value, and output an alert to the user when the estimated eye blink frequency is less than or equal to the preset reference value.

2. The dry eye syndrome alert system through posture and work detection of claim 1, wherein the data collecting unit includes:
a sensor unit configured to detect the posture of the user to collect the posture data of the user; and
a preprocessing unit configured to preprocess the posture data.

3. The dry eye syndrome alert system through posture and work detection of claim 2, wherein the eye blink frequency calculating unit includes:
a motion variability calculating unit configured to identify the posture change of the user on the basis of the posture data and calculate the motion variability on the basis of the posture change; and
an eye blink frequency estimating unit configured to estimate the eye blink frequency of the user on the basis of the motion variability.

4. The dry eye syndrome alert system through posture and work detection of claim 3, wherein the diagnosis and alert output unit includes:
a diagnosis unit configured to store frequency data regarding the estimated eye blink frequency and compare the frequency data with the preset reference value to determine whether the estimated eye blink frequency is less than or equal to the preset reference value; and
an alert output unit configured to output the alert to the user when the estimated eye blink frequency is less than or equal to the preset reference value.

5. The dry eye syndrome alert system through posture and work detection of claim 3, wherein the sensor unit includes:
a plurality of pressure sensors disposed on a seat of a chair; and
a plurality of distance sensors disposed on a backrest of the chair.

6. The dry eye syndrome alert system through posture and work detection of claim 5, wherein the motion variability calculating unit calculates the motion variability of the user on the basis of a change in pressure data measured through the plurality of pressure sensors and interval data between a back of the user and the backrest measured through the plurality of distance sensors.

7. The dry eye syndrome alert system through posture and work detection of claim 3, wherein the eye blink frequency estimating unit estimates the eye blink frequency of the user by matching the motion variability with eye blink frequency quantified data that is stored in advance.

8. The dry eye syndrome alert system through posture and work detection of claim 4, wherein the alert output unit is disposed on any one of an armrest of a chair and a smart device of the user.

* * * * *